United States Patent
Willyard et al.

(10) Patent No.: US 10,251,701 B2
(45) Date of Patent: *Apr. 9, 2019

(54) FLOW RATE VERIFICATION MONITOR FOR FLUID-COOLED MICROWAVE ABLATION PROBE

(71) Applicant: COVIDIEN LP, Mansfield, MA (US)

(72) Inventors: Richard A. Willyard, Berthoud, CO (US); Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,500

(22) Filed: May 15, 2017

(65) Prior Publication Data
US 2017/0245932 A1     Aug. 31, 2017

Related U.S. Application Data

(63) Continuation of application No. 14/923,486, filed on Oct. 27, 2015, now Pat. No. 9,668,812, which is a (Continued)

(51) Int. Cl.
*A61B 18/18* (2006.01)
*A61B 18/00* (2006.01)

(52) U.S. Cl.
CPC ............... *A61B 18/1815* (2013.01); *A61B 2018/00023* (2013.01); *A61B 2018/00577* (2013.01);
(Continued)

(58) Field of Classification Search
CPC ............... A61B 18/18; A61B 18/1815; A61B 2018/1838; A61B 2018/1861;
(Continued)

(56) References Cited

U.S. PATENT DOCUMENTS

D263,020 S    2/1982    Rau, III
D295,893 S    5/1988    Sharkany et al.
(Continued)

FOREIGN PATENT DOCUMENTS

CN    1103807 C    3/2003
DE    390937 C     3/1924
(Continued)

OTHER PUBLICATIONS

European Search Report EP 07253835.8 dated Dec. 20, 2007.
(Continued)

*Primary Examiner* — Thomas Giuliani
(74) *Attorney, Agent, or Firm* — Carter, DeLuca & Farrell, LLP

(57) ABSTRACT

A microwave ablation system includes an antenna assembly configured to deliver microwave energy from an energy source to tissue and a coolant source operably coupled to the energy source and configured to selectively provide fluid to the antenna assembly via a fluid path. The system also includes a controller operably coupled to the energy source and a piezoelectric transducer operably coupled to the fluid path to detect a force of fluid flow through the fluid path. The piezoelectric transducer is configured to generate a signal based on the detected force of fluid through the fluid path. The controller is configured to control the energy source output based on the generated signal.

16 Claims, 4 Drawing Sheets

Related U.S. Application Data continuation of application No. 12/786,671, filed on May 25, 2010, now Pat. No. 9,192,436.

(52) U.S. Cl.
CPC ............ *A61B 2018/00702* (2013.01); *A61B 2018/00863* (2013.01); *A61B 2018/1823* (2013.01)

(58) Field of Classification Search
CPC .. A61B 2018/1869; A61B 2018/00005; A61B 2018/00011; A61B 2018/00023; A61B 2018/1823; A61B 2018/00863; A61B 2018/00702; A61B 2018/00577
USPC .......... 606/33, 38, 41, 42; 607/99, 101, 104, 607/105, 113, 115, 116, 154, 156
See application file for complete search history.

(56) References Cited

U.S. PATENT DOCUMENTS

| | | |
|---|---|---|
| D295,894 S | 5/1988 | Sharkany et al. |
| 5,231,997 A | 8/1993 | Kikuchi et al. |
| 5,829,519 A | 11/1998 | Uthe |
| 6,007,571 A | 12/1999 | Neilson et al. |
| D424,694 S | 5/2000 | Tetzlaff et al. |
| D425,201 S | 5/2000 | Tetzlaff et al. |
| D449,886 S | 10/2001 | Tetzlaff et al. |
| 6,350,276 B1 | 2/2002 | Knowlton |
| D457,958 S | 5/2002 | Dycus et al. |
| D457,959 S | 5/2002 | Tetzlaff et al. |
| D496,997 S | 10/2004 | Dycus et al. |
| D499,181 S | 11/2004 | Dycus et al. |
| 6,978,779 B2 * | 12/2005 | Haveri .............. A61M 15/0085 128/200.14 |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| 7,160,296 B2 | 1/2007 | Pearson et al. |
| D541,418 S | 4/2007 | Schechter et al. |
| D541,938 S | 5/2007 | Kerr et al. |
| 7,311,703 B2 | 12/2007 | Turovskiy et al. |
| D564,662 S | 3/2008 | Moses et al. |
| 7,344,533 B2 | 3/2008 | Pearson et al. |
| 7,469,593 B2 | 12/2008 | Zumberge et al. |
| D613,412 S | 4/2010 | DeCarlo |
| 7,863,984 B1 | 1/2011 | Behnke |
| 7,963,785 B2 | 6/2011 | Arts et al. |
| 8,038,693 B2 | 10/2011 | Allen |
| 8,069,553 B2 | 12/2011 | Bonn |
| 8,118,808 B2 | 2/2012 | Smith et al. |
| 8,188,435 B2 | 5/2012 | Podhajsky et al. |
| 8,197,473 B2 | 6/2012 | Rossetto et al. |
| 8,202,270 B2 | 6/2012 | Rossetto et al. |
| 8,216,227 B2 | 7/2012 | Podhajsky |
| 8,235,981 B2 | 8/2012 | Prakash et al. |
| 8,282,632 B2 | 10/2012 | Rossetto |
| 8,292,881 B2 | 10/2012 | Brannan et al. |
| 8,313,486 B2 | 11/2012 | Kim et al. |
| 8,328,799 B2 | 12/2012 | Brannan |
| 8,328,800 B2 | 12/2012 | Brannan |
| 8,328,801 B2 | 12/2012 | Brannan |
| 8,334,812 B2 | 12/2012 | Brannan |
| 8,343,145 B2 | 1/2013 | Brannan |
| 8,353,903 B2 | 1/2013 | Podhajsky |
| 8,355,803 B2 | 1/2013 | Bonn et al. |
| 8,382,750 B2 | 2/2013 | Brannan |
| 8,394,087 B2 | 3/2013 | Willyard et al. |
| 8,394,092 B2 | 3/2013 | Brannan |
| 8,409,187 B2 | 4/2013 | Bonn |
| 8,409,188 B2 | 4/2013 | Kim et al. |
| 8,430,871 B2 | 4/2013 | Brannan |
| 8,463,396 B2 | 6/2013 | Podhajsky |
| 8,469,953 B2 | 6/2013 | DeCarlo |
| 8,491,579 B2 | 7/2013 | Rossetto |
| 8,545,493 B2 | 10/2013 | Brannan et al. |
| 8,552,915 B2 | 10/2013 | Brannan |
| 8,556,889 B2 | 10/2013 | Brannan |
| 8,568,398 B2 | 10/2013 | Brannan |
| 8,568,401 B2 | 10/2013 | Brannan |
| 8,568,404 B2 | 10/2013 | Brannan |
| 8,617,153 B2 | 12/2013 | Lee et al. |
| 8,652,127 B2 | 2/2014 | Prakash et al. |
| 8,672,923 B2 | 3/2014 | Ladtkow et al. |
| 8,672,933 B2 | 3/2014 | Shiu et al. |
| 8,764,744 B2 | 7/2014 | Brannan |
| 8,777,939 B2 | 7/2014 | Lee et al. |
| 8,834,460 B2 | 9/2014 | Peterson |
| 8,876,814 B2 | 11/2014 | Bonn |
| 8,882,759 B2 | 11/2014 | Manley et al. |
| 8,906,007 B2 | 12/2014 | Bonn et al. |
| 8,968,288 B2 | 3/2015 | Brannan |
| 9,024,237 B2 | 5/2015 | Bonn |
| 9,028,474 B2 | 5/2015 | Brannan et al. |
| 9,031,668 B2 | 5/2015 | DeCarlo |
| 9,095,359 B2 | 8/2015 | Behnke, II et al. |
| 9,113,925 B2 | 8/2015 | Smith et al. |
| 9,113,926 B2 | 8/2015 | Brannan et al. |
| 9,113,927 B2 | 8/2015 | Kim et al. |
| 9,192,436 B2 * | 11/2015 | Willyard ............ A61B 18/1815 |
| 9,241,762 B2 | 1/2016 | Podhajsky et al. |
| 9,277,969 B2 | 3/2016 | Brannan et al. |
| 9,375,273 B2 | 6/2016 | Brannan et al. |
| 9,377,367 B2 | 6/2016 | Podhajsky et al. |
| 9,468,492 B2 | 10/2016 | Podhajsky et al. |
| 9,561,076 B2 | 2/2017 | Brannan et al. |
| 9,668,812 B2 * | 6/2017 | Willyard ............ A61B 18/1815 |
| 2002/0169445 A1 | 11/2002 | Jain et al. |
| 2005/0245920 A1 | 11/2005 | Vitullo et al. |
| 2006/0015162 A1 | 1/2006 | Edward et al. |
| 2008/0269737 A1 | 10/2008 | Elmouelhi et al. |
| 2009/0030411 A1 | 1/2009 | Werneth et al. |
| 2009/0131926 A1 | 5/2009 | Rusin et al. |
| 2010/0016756 A1 | 1/2010 | Tahar |
| 2010/0092939 A1 | 4/2010 | Belous et al. |
| 2010/0262134 A1 | 10/2010 | Jensen et al. |
| 2010/0268223 A1 | 10/2010 | Coe et al. |
| 2010/0268225 A1 | 10/2010 | Coe et al. |
| 2010/0331834 A1 | 12/2010 | Peterson et al. |
| 2011/0054458 A1 | 3/2011 | Behnke |
| 2011/0054459 A1 | 3/2011 | Peterson |
| 2011/0077637 A1 | 3/2011 | Brannan |
| 2011/0077638 A1 | 3/2011 | Brannan |
| 2011/0118723 A1 * | 5/2011 | Turner ............... A61B 18/1815 606/33 |
| 2011/0118731 A1 | 5/2011 | Ladtkow |
| 2011/0172659 A1 | 7/2011 | Brannan |
| 2011/0208180 A1 | 8/2011 | Brannan |
| 2011/0213353 A1 | 9/2011 | Lee et al. |
| 2011/0238055 A1 | 9/2011 | Kim et al. |
| 2011/0270240 A1 | 11/2011 | Shiu et al. |
| 2011/0301589 A1 | 12/2011 | Podhajsky et al. |
| 2011/0319880 A1 | 12/2011 | Prakash et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1238263 B | 4/1967 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |

(56) References Cited

FOREIGN PATENT DOCUMENTS

| | | |
|---|---|---|
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 246350 A1 | 11/1987 |
| EP | 0521264 A2 | 1/1993 |
| EP | 556705 A1 | 8/1993 |
| EP | 0558429 A1 | 9/1993 |
| EP | 836868 A2 | 4/1998 |
| EP | 882955 A1 | 12/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 9706739 A2 | 2/1997 |
| WO | 9706740 A2 | 2/1997 |
| WO | 9706855 A2 | 2/1997 |
| WO | 9743971 A2 | 11/1997 |
| WO | 0048672 A1 | 8/2000 |
| WO | 2010035831 A1 | 4/2010 |

OTHER PUBLICATIONS

European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
U.S. Appl. No. 08/483,742, filed Jun. 7, 1995.
U.S. Appl. No. 08/136,098, filed Oct. 14, 1993.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Esterline, "Light Key Projection Keyboard" Advanced Input Systems, located at: <http://www.advanced-input.com/lightkey> 2002.
Urologix, Inc.—Medical Professionals: Targis.TM. Technology, "Overcoming the Challenge" located at: <http://www.urologix.com!medicaUtechnology.html> Nov. 18, 1999; 3 pages.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.

(56) References Cited

OTHER PUBLICATIONS

European Search Report EP 05023017.6 dated Feb. 24, 2006.
European Search Report EP 050254214 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite.cndot.Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).

(56) References Cited

OTHER PUBLICATIONS

Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.

(56) References Cited

OTHER PUBLICATIONS

C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw. cndot.Hill, vol. 111, (1984), pp. 2490-2499.
Cosman et al., "Radiofrequency Lesion Generation and its Effect on Tissue Impedence", Applied Neurophysiology, 51:230-242, 1988.

Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.

\* cited by examiner

FLOW RATE VERIFICATION MONITOR FOR FLUID-COOLED MICROWAVE ABLATION PROBE

CROSS-REFERENCE TO RELATED APPLICATIONS

This application is a continuation application of U.S. patent application Ser. No. 14/923,486 filed on Oct. 27, 2015, now U.S. Pat. No. 9,668,812, which is a continuation application of U.S. patent application Ser. No. 12/786,671 filed on May 25, 2010, now U.S. Pat. No. 9,192,436, the entire contents of each of which are incorporated herein by reference.

BACKGROUND

Technical Field

The present disclosure relates generally to microwave ablation procedures that utilize microwave surgical devices having a microwave antenna that may be inserted directly into tissue for diagnosis and treatment of diseases. More particularly, the present disclosure is directed to a system and method for monitoring correct system operation of a microwave ablation system utilizing a piezoelectric device.

Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 300 MHz to about 10 GHz is applied to a targeted tissue site to create an ablation volume, which may have a particular size and shape. Ablation volume is correlated to antenna design, antenna performance, antenna impedance, and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

Microwave ablation devices utilize sensors to determine if the system is working properly. However, without delivery of microwave energy, the sensors may indicate that the probe assembly status is normal. Further, defects in antenna assemblies may not be apparent except at high powers. As such, when microwave ablation system is tested using a low power routine a post manufacture defect may not be apparent. This is especially important for high power microwave ablation devices, where failures may result in extremely high temperatures.

Fluid-cooled or dielectrically-buffered microwave ablation devices may also be used in ablation procedures to cool the microwave ablation probe. Cooling the ablation probe may enhance the overall ablation pattern of antenna, and/or prevent damage to the antenna. However, during operation of the microwave ablation device, if the flow of coolant or buffering fluid is interrupted, the microwave ablation device may exhibit rapid failures due to the heat generated from the increased reflected power.

SUMMARY

According to an embodiment of the present disclosure, a microwave ablation system includes an antenna assembly configured to deliver microwave energy from an energy source to tissue and a coolant source operably coupled to the energy source and configured to selectively provide fluid to the antenna assembly via a fluid path. The system also includes a controller operably coupled to the energy source and a piezoelectric transducer operably coupled to the fluid path to detect a force of fluid flow through the fluid path. The piezoelectric transducer is configured to generate a signal based on the detected force of fluid through the fluid path. The controller is configured to control the energy source output based on the generated signal.

According to another embodiment of the present disclosure, a microwave ablation system includes an antenna assembly configured to deliver microwave energy from an energy source to tissue and a coolant source operably coupled to the energy source and configured to selectively provide fluid to the antenna assembly via a fluid path. The system also includes a controller operably coupled to the energy source and an insert disposed within the fluid path and configured to impart a force on a piezoelectric transducer operably coupled to the antenna assembly that is substantially equal to a force of fluid flow through the fluid path. The piezoelectric transducer is configured to generate a signal based on the force imparted thereon by the insert. The controller is configured to control the energy source output based on a comparison between the generated signal and a predetermined range.

The present disclosure also provides for a method of detecting fluid flow through a microwave ablation system. The method includes the steps of delivering microwave energy from a power source to tissue via an antenna assembly and supplying fluid from a coolant source to the antenna assembly via a fluid path. The method also includes the steps of detecting a force of fluid flow through the fluid path via a piezoelectric transducer and generating an electric signal based on the detected force of fluid flow through the fluid path. The method also includes the steps of comparing the generated signal to a predetermined range and modifying output of energy from the energy source based on the comparison between the detected force of fluid flow through the fluid path and the predetermined range.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
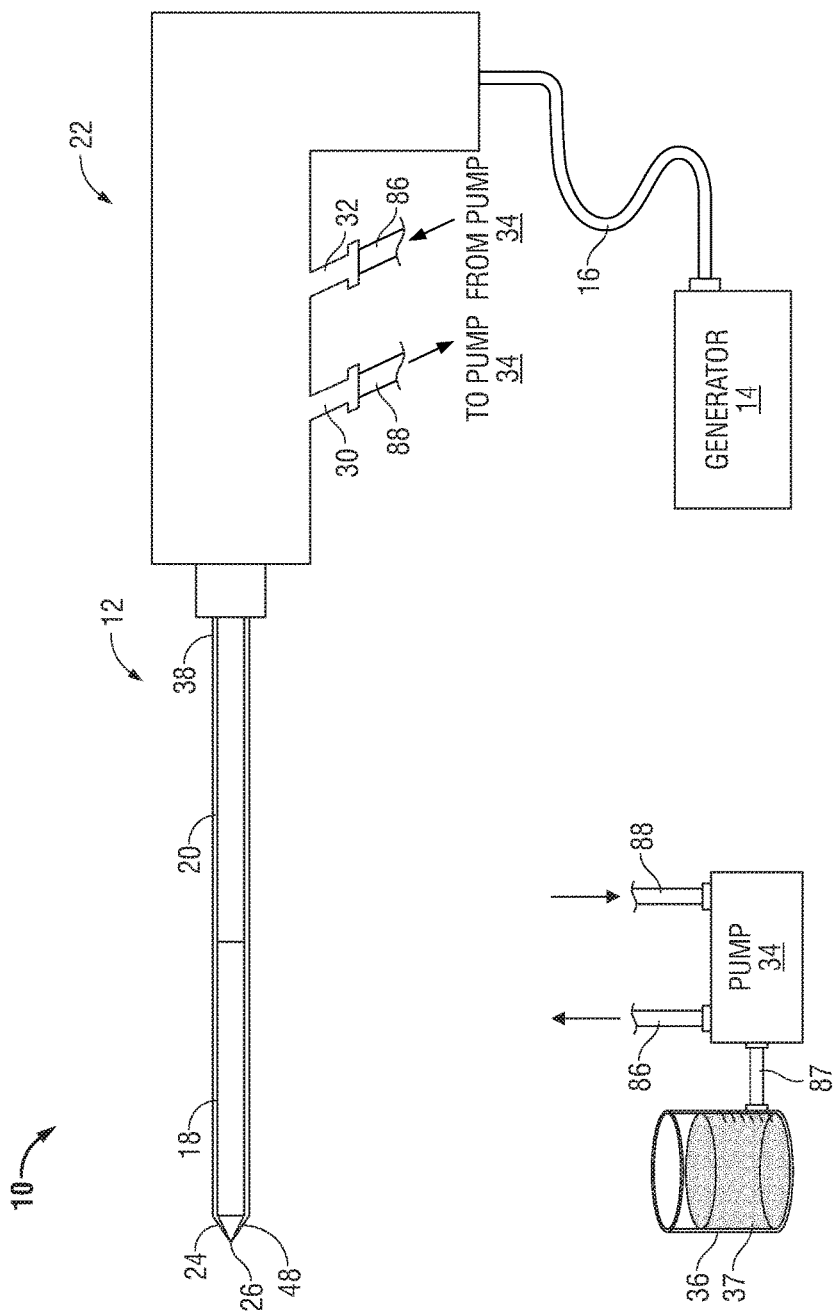
FIG. 1 shows a diagram of a microwave antenna assembly in accordance with an embodiment of the present disclosure.

Embodiments of the presently disclosed apparatus are described in detail below with reference to the drawings wherein like reference numerals identify similar or identical elements in each of the several views. In the discussion that follows, the term "proximal" will refer to the portion of a structure that is closer to a user, while the term "distal" will refer to the portion of the structure that is farther from the user.

Generally, the present disclosure is directed to a microwave antenna assembly having an energy source or generator adapted to deliver energy to tissue via the antenna assembly and a coolant source for circulating a dielectric coolant fluid through the microwave antenna assembly. More particularly, the present disclosure is directed to monitoring fluid flow through the microwave antenna assembly and controlling the energy source output based on the monitored fluid flow to prevent damage to the antenna and/or harm to the clinician or patient caused by overheating of the antenna assembly.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 300 MHz to about 6000 MHz, although other suitable frequencies are also contemplated.

In the illustrated embodiment, the antenna assembly 12 includes a radiating portion 18 connected by feedline 20 (or shaft) to the cable 16. More specifically, the antenna assembly 12 is coupled to the cable 16 through a handle enclosure 22 having an outlet fluid port 30 and an inlet fluid port 32 that are connected in fluid communication with a sheath 38. The sheath 38 encloses radiating portion 18 and feedline 20 to form a chamber 89 (FIG. 2) allowing a coolant fluid 37 to circulate about the antenna assembly 12. The ports 30 and 32 are also coupled to a supply pump 34 via supply lines 88 and 86, respectively. Supply pump 34 is, in turn, coupled to a supply tank 36 via a supply line 87. The supply pump 34 may be a peristaltic pump or any other suitable type. The supply tank 36 stores the coolant fluid 37 and, in one embodiment, may maintain the fluid 37 at a predetermined temperature. More specifically, the supply tank 36 may include a coolant unit that cools the returning liquid from the antenna assembly 12. In another embodiment, the coolant fluid 37 may be a gas and/or a mixture of fluid and gas.

Figure 2:
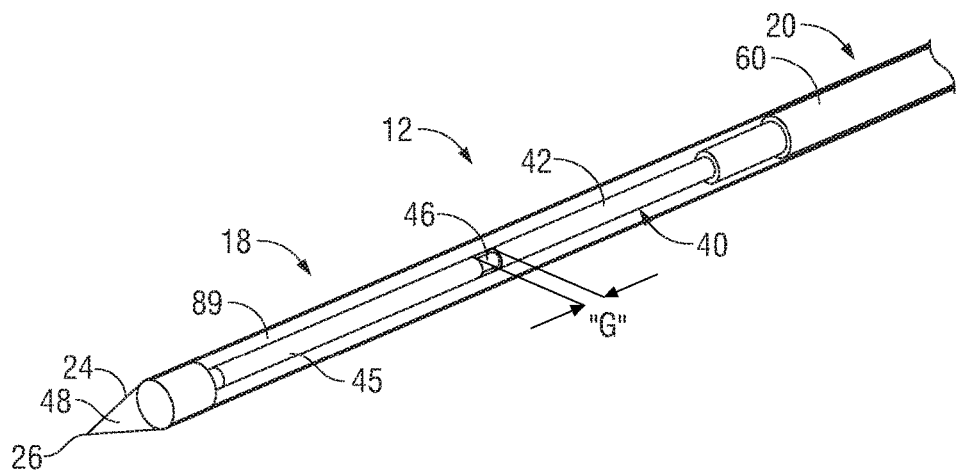
FIG. 2 shows a perspective view of a distal end of the microwave antenna assembly of FIG. 1.

FIG. 2 illustrates the radiating portion 18 of the antenna assembly 12 having a dipole antenna 40. The dipole antenna 40 is coupled to the feedline 20 that electrically connects antenna assembly 12 to the generator 14. The dipole antenna 40 includes a proximal portion 42 and a distal portion 45 interconnected at a feed point 46. The distal portion 45 and the proximal portion 42 may be either balanced (e.g., of equal lengths) or unbalanced (e.g., of unequal lengths). A dipole feed gap "G" is disposed between the proximal and distal portions 42 and 45 at the feed point 46. The gap "G" may be from about 1 mm to about 3 mm. In one embodiment, the gap "G" may be thereafter filled with a dielectric material at the feed point 46. The dielectric material may be polytetrafluoroethylene (PTFE), such as Teflon® sold by DuPont of Willmington, Del. In another embodiment, the gap "G" may be coated with a dielectric seal coating. The antenna assembly 12 also includes a choke 60 disposed around the feedline 20. The choke 60 may be a quarter-wavelength shorted choke that is shorted to the feedline 20 at the proximal end (not illustrated) of the choke 60 by soldering or other suitable methods.

Assembly 12 also includes a tip 48 at a distal end of the radiating portion 18 having a tapered end 24 that terminates, in one embodiment, at a pointed end 26 to allow for insertion into tissue with minimal resistance. In those cases where the radiating portion 18 is inserted into a pre-existing opening, tip 48 may be rounded or flat. The tip 48 may be formed from a variety of heat-resistant materials suitable for penetrating tissue, such as metals (e.g., stainless steel) and various thermoplastic materials, such as poletherimide, and polyamide thermoplastic resins.

Figure 3:
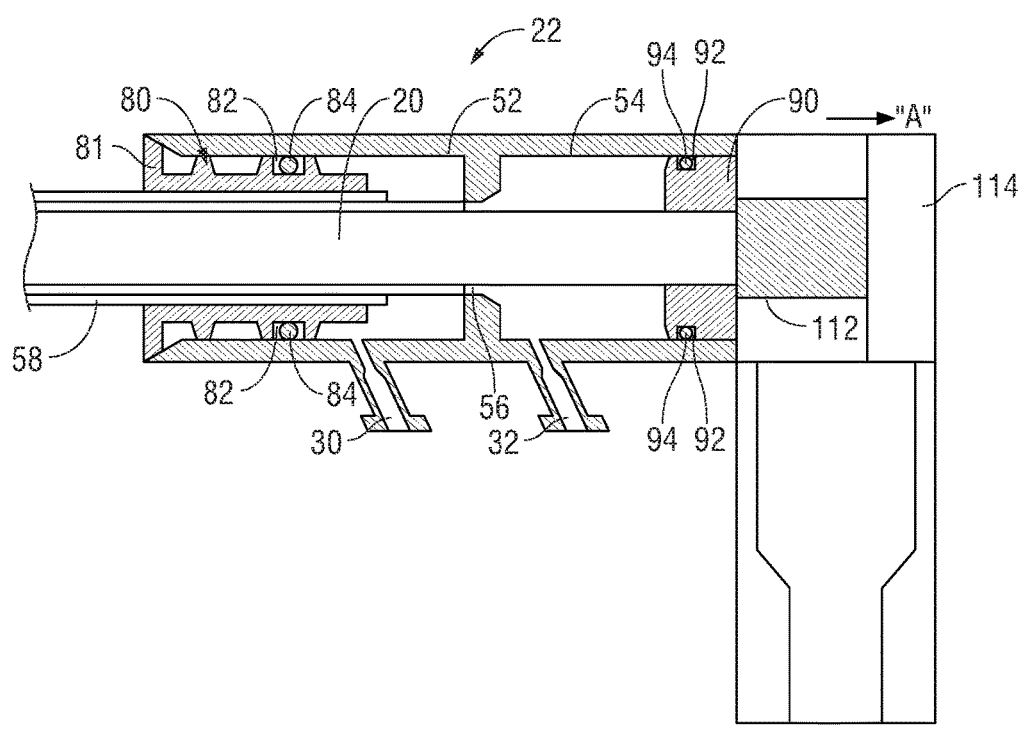
FIG. 3 shows a cross-sectional view of a proximal end of the microwave antenna assembly of FIG. 1.

FIG. 3 illustrates a cross-sectional view of the handle enclosure 22 of FIG. 1. Handle enclosure 22 houses an outflow chamber 52 disposed distal to an inflow chamber 54. Outflow chamber 52 and inflow chamber 54 are in fluid communication through an interconnecting lumen 56 that extends distally from a distal end of inflow chamber 54 and that houses at least a portion of the longitudinal length of feedline 20 and/or radiating portion 18. As shown in FIG. 3, feedline 20 extends distally through interconnecting lumen 56 through outflow chamber 52 and into inflow chamber 54. Outflow chamber 52 is in fluid communication with outlet fluid port 30 and inflow chamber 54 is in fluid communication with inlet fluid port 32. A return lumen 58 is disposed along at least a longitudinal portion of feedline 20 to surround at least a portion of interconnecting lumen 56 and provides fluid communication between chamber 89 and outflow chamber 52 to return coolant fluid 37 from chamber 89 to the pump 34 via outlet fluid port 30.

A distal insert 80 is disposed within outflow chamber 52 and surrounds feedline 20 along at least a portion of the longitudinal length thereof. Insert 80 is disposed at a distal end of outflow chamber 52 and defines a distal cap 81 that fluidly seals a distal end of handle enclosure 22 to prevent contaminants from entering handle enclosure 22 through outflow chamber 52. Insert 80 includes a recessed portion 82 about which an o-ring 84 is disposed to fluidly seal a portion of outflow chamber 52 that is disposed distal to outlet fluid port 30, as shown in FIG. 3.

A proximal insert 90 is disposed within inflow chamber 54 and surrounds feedline 20 along at least a portion of the longitudinal length thereof. Insert 90 abuts a proximal end of the inflow chamber 54 and includes a recessed portion 92 about which an o-ring 94 is disposed to fluidly seal a portion of inflow chamber 54 that is disposed proximal to inlet fluid port 32.

During circulation of coolant fluid 37 throughout antenna assembly 12, there exists a fluid pressure differential between the outflow chamber 52 and the inflow chamber 54. In particular, fluid pressure within the inflow chamber 54 (e.g., about 50 psi) is typically greater than fluid pressure within the outflow chamber 52 (e.g., about 0 psi). The flow of coolant fluid 37 through antenna assembly 12 may be monitored by sensing the fluid pressure that exists within the inflow chamber 54 to ensure adequate circulation of coolant fluid 37 within antenna assembly 12 during operation thereof, as will be described in more detail below.

A piezoelectric transducer 112 may be disposed between insert 90 and an abutment portion 114 of handle enclosure 22 such that transducer 112 abuts at a distal end the insert 90 and at a proximal end the abutment portion 114. Piezoelectric transducer 112 includes a suitable active material (e.g., piezoelectric ceramic, crystal, etc.) disposed between a pair of conductive elements (not explicitly shown) that generates a voltage when a mechanical stress is imparted thereon. The generated voltage between the conductive elements operates to mechanically deform the active material, thereby generating an electric field or electric signal. In this manner, transducer 112 may operate as a sensing component as well as a transmitting component. Transducer 112 transmits the electric signal to the generator 14 through any suitable electrical connection and, based on the received electric signal, the generator 14 automatically controls the operation of the ablation system 10, as discussed in greater detail below.

Since the components of inflow chamber 54 (e.g., insert 90) are not mechanically locked in place, the fluid pressure within inflow chamber 54 operates to impart a force substantially equally in all directions within inflow chamber 54 including in the proximal direction depicted by directional arrow "A" in FIG. 3. For example, the fluid pressure generated by coolant fluid 37 imparts a force on insert 90 in the direction of directional arrow "A" that is substantially equal to the fluid pressure within inflow chamber 54. This force imparted on insert 90 causes insert 90, in turn, to impart a substantially equal force on transducer 112 in the direction of arrow "A". In response thereto, transducer 112 generates an electric field or signal to the generator 14 for controlling operation of the ablation system 10, as described in further detail below. In some embodiments, handle enclosure 22 may include any suitable mechanical components (e.g., ribs, inserts, washers, gaskets, buffers, locking components, grooves, springs, linkages, etc.) adapted to suppress or eliminate the effects of extraneous or ancillary forces (e.g., forces other than those described above) that may be transferred to or imparted on transducer 112 such as, for example, forces generated by the insertion and/or extraction of antenna assembly 12 relative to tissue. In this manner, forces imparted on and sensed by the transducer 112 are true to the fluid pressure within inflow chamber 54 due to the above-described suppression and/or elimination of extraneous forces.

Figure 4:
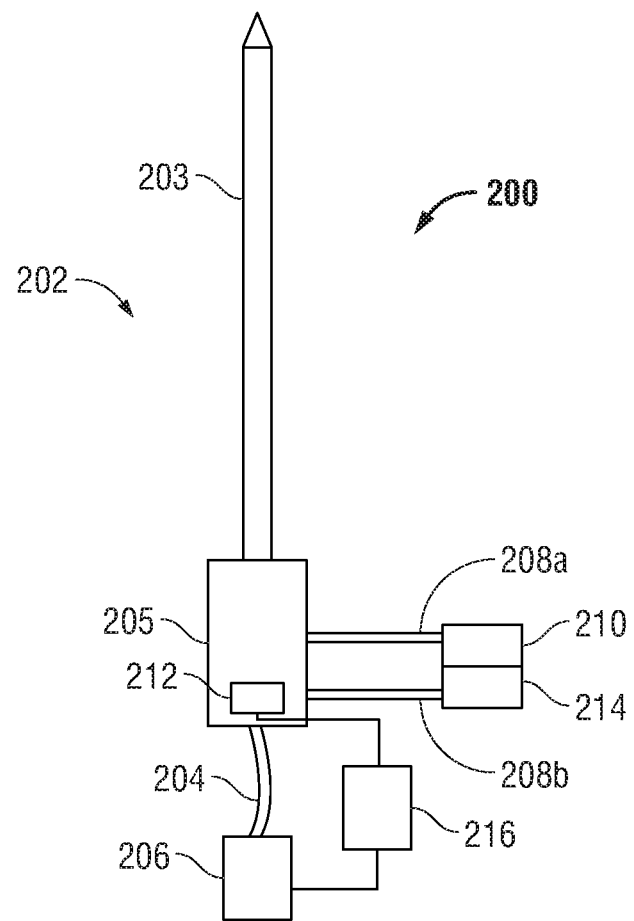
FIG. 4 shows a system block diagram of a microwave antenna assembly according to another embodiment of the present disclosure.

With reference to FIG. 4, a microwave ablation system, shown generally as 200, according to an embodiment of the present disclosure is depicted. The system 200 includes an ablation device 202 having an antenna 203 and a handle 205 used to ablate tissue. A generator 206, which is substantially similar to power generating source 28, supplies the ablation device 202 with energy via coaxial cable 204. Ablation device is supplied with coolant or fluid from coolant supply 210 through inflow conduit 208a. The coolant fluid 37 flows through the ablation device 202 as described above and exits the ablation device via outflow conduit 208a into chamber 214. In some embodiments, conduits 208a and 208b may be replaced by a single multi-lumen conduit (not shown) having an inflow lumen for supplying the ablation device 202 with coolant and an outflow lumen for coolant to exit the ablation device 202 into the chamber 214.

As shown in FIG. 4, the microwave ablation system 200 includes a piezoelectric transducer 212 disposed in the handle 205 and configured to sense fluid pressure, as described above with respect to the embodiment of FIG. 3, for monitoring the flow rate of fluid through ablation system 200. As described above, when coolant circulation is interrupted, the ablation device tends to exhibit rapid failures. Further, when coolant circulation is too great and/or the flow rate of fluid exceeds a predetermined threshold maximum (e.g., 100 ml/min, 130 ml/min, etc.), the ablation device may be exhibiting symptoms of a fluid leak. By monitoring the flow of coolant fluid 37 through microwave ablation system 200, damage to the ablation device may be prevented.

Controller 216 is coupled to generator 206 and is configured to control generator 206 based on an input or signal received from transducer 212. Controller 216 may be a microprocessor or any suitable logic circuit able to receive an input or signal from transducer 212 and provide an output to control generator 206. Controller 216 may be operably coupled to a storage device or memory (not shown) configured to store programmable instructions, historical data, lookup tables, operating parameters, etc.

Transducer 212 may be a single device or an array of devices configured to detect operational parameters of the ablation device 202 in order to determine if the microwave ablation system 200 is functioning properly. In use, transducer 212 provides an electrical signal to the controller 216 that represents a real-time measurement or indication of fluid pressure. In some embodiments, a suitable time delay may be utilized by transducer 212 in sending the electrical signal to controller 216 such that momentary pressure transients that may occur during initial pressurization of system 200 are ignored. Controller 216 compares the electrical signal to a predetermined range. If the electrical signal is within the predetermined range, the controller 216 controls the generator 206 to continue with the ablation procedure and/or the supply ablation energy to ablation device 202. If the electrical signal is outside the predetermined range, the controller 216 controls the generator 206 to cease the ablation procedure and/or modify generator 206 output. For example, the predetermined range may be a range of fluid pressures within inflow chamber 54 (See FIG. 3) or through conduit 208a (See FIG. 5A). In one embodiment, the predetermined range of fluid pressure requirements is between about 25 psi and about 100 psi. In this scenario, the operating range of fluid pressure may be between about 35 psi and about 40 psi.

Transducer 212 may be incorporated into ablation device 202, as depicted by the illustrated embodiment, or may be coupled to ablation device 202 and/or controller 216. Transducer 212 may be placed anywhere along the fluid path of ablation system 200. For instance, transducer 212 may be placed in antenna 203, handle 205, or along the inflow conduit 208a (See FIG. 5A). The transducer 212 is configured to detect fluid pressure caused by fluid flow during startup (e.g., before microwave energy is delivered to the ablation device 202) or during an ablation procedure.

Figure 5A:
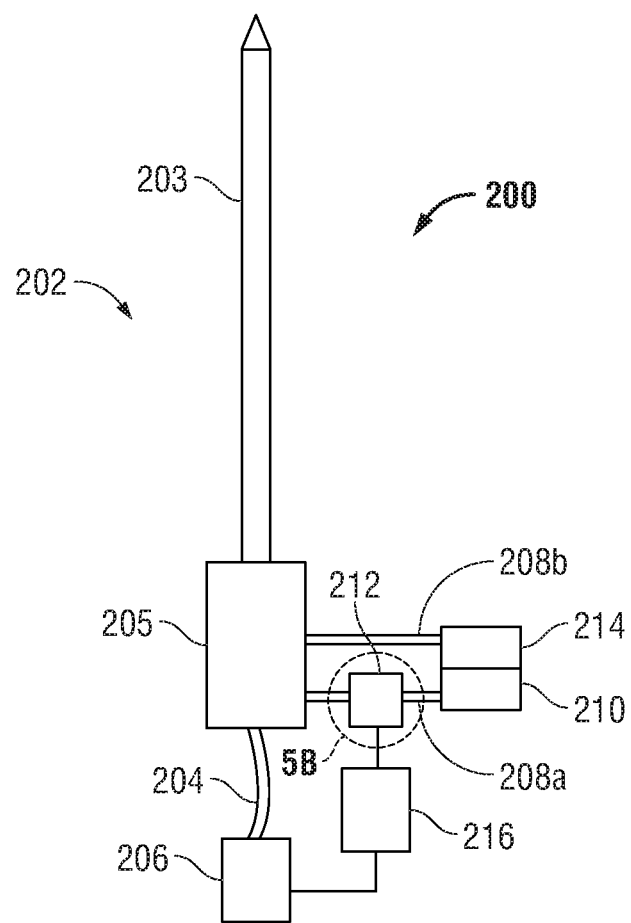
FIG. 5A shows a system block diagram of a microwave antenna assembly according to another embodiment of the present disclosure.
Figure 5B:
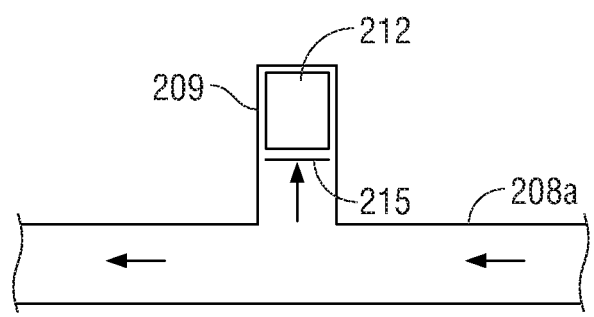
FIG. 5B shows the area of detail of FIG. 5A according to an embodiment of the present disclosure.

In another embodiment shown in FIG. 5A, piezoelectric transducer 212 is operably coupled to inflow conduit 208a to sense fluid pressure therethrough. In this scenario, transducer 212 is configured to operate in conjunction with microwave ablation system 200 as substantially described above with reference to FIG. 4 and will only be described to the extent necessary to explain the differences between the embodiments. In particular, as shown in FIG. 5B, transducer 212 is disposed within a cylinder 209 in fluid communication with inflow conduit 208a. In the illustrated embodiment, for example, cylinder 209 may be disposed substantially perpendicular to the fluid flow within inflow conduit 208a. When sufficient fluid flow exists through inflow conduit 208a, as depicted by directional arrows in FIG. 5B, coolant fluid 37 flows into cylinder 209 to impart a force on an insert or piston membrane 215, thereby causing piston membrane 215 to move within cylinder and translate a corresponding force on transducer 212. Piston membrane 215 may be substantially equal in diameter to the inner periphery of cylinder 209 to facilitate sliding movement of piston membrane 215 within cylinder 209 in a so-called "cylinder-piston" relationship. That is, piston membrane 215 may slide within cylinder 209 and generate a friction force on the inner surface of cylinder 209. As described above with respect to the embodiment of FIG. 4, transducer 212 provides an electrical signal to the controller 216 that represents a real-time measurement or indication of fluid pressure. Controller 216 is coupled to generator 206 and is configured to control generator 206 based on the signal received from transducer 212.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave antenna assembly, comprising:
   a handle including an abutment portion and housing a first fluid chamber disposed distal to the abutment portion and a second fluid chamber disposed distal to the first fluid chamber;
   a feedline extending through the handle and configured to deliver microwave energy to tissue;
   a fluid lumen surrounding the feedline and configured to receive a coolant fluid, the fluid lumen disposed in fluid communication with the first fluid chamber; and
   a piezoelectric transducer disposed within the handle between the abutment portion and the first fluid chamber and configured to abut the abutment portion and detect a force of fluid flow through the first fluid chamber.

2. The microwave antenna assembly according to claim 1, wherein the feedline extends through the first and second fluid chambers.

3. The microwave antenna assembly according to claim 1, wherein the first fluid chamber is in fluid communication with the second fluid chamber.

4. The microwave antenna assembly according to claim 1, further comprising a movable insert disposed within the first fluid chamber and configured to impart a force on the piezoelectric transducer.

5. The microwave antenna assembly according to claim 1, further comprising a return lumen disposed along at least a portion of the feedline to provide fluid communication between the fluid lumen and the second fluid chamber.

6. The microwave antenna assembly according to claim 1, wherein the first fluid chamber is configured to receive cooling fluid from a fluid source and the second fluid chamber is configured to deliver cooling fluid from the microwave antenna assembly to the fluid source.

7. The microwave assembly according to claim 1, wherein the feedline includes an inner conductor, an outer conductor disposed about the inner conductor, and a dielectric material disposed between the inner conductor and the outer conductor.

8. The microwave antenna assembly according to claim 7, wherein the inner conductor is disposed within the fluid lumen.

9. The microwave antenna assembly according to claim 1, further comprising an insert disposed within the second fluid chamber and configured to fluidly seal a distal portion of the handle.

10. The microwave antenna assembly according to claim 1, further comprising an interconnecting fluid lumen surrounding the feedline and configured to provide fluid communication between the first and second fluid chambers.

11. A microwave antenna assembly, comprising:
a handle;
a first fluid chamber disposed within the handle;
a second fluid chamber disposed within the handle distal to and in fluid communication with the first fluid chamber;
a feedline extending through the first and second fluid chambers and configured to deliver microwave energy to tissue;
a fluid lumen surrounding a portion of the feedline and configured to receive a coolant fluid, the fluid lumen in fluid communication with the first fluid chamber; and
a piezoelectric transducer disposed within the handle between the first fluid chamber and an abutment portion of the handle disposed proximal to the first fluid chamber, the piezoelectric transducer configured to detect a force of fluid flow through the first chamber.

12. The microwave antenna assembly according to claim 11, wherein the fluid lumen is disposed between the feedline and a sheath surrounding at least a portion of the feedline.

13. The microwave antenna assembly according to claim 11, further comprising an interconnecting fluid lumen surrounding a portion of the feedline and configured to provide fluid communication between the first and second fluid chambers.

14. The microwave antenna assembly according to claim 11, further comprising a movable insert disposed within the first fluid chamber and configured to impart a force on the piezoelectric transducer.

15. The microwave antenna assembly according to claim 11, further comprising a return lumen disposed along at least a portion of the feedline to provide fluid communication between the fluid lumen and the second fluid chamber.

16. A handle for a microwave antenna assembly, comprising:
an abutment portion;
a first fluid chamber disposed distal to the abutment portion and proximal to and in fluid communication with a second fluid chamber;
a fluid lumen configured to receive a coolant fluid for cooling a feedline, the fluid lumen in fluid communication with the first fluid chamber; and
a piezoelectric transducer disposed between the abutment portion and the first fluid chamber within the handle and configured to abut the abutment portion and detect a force of fluid flow through the first chamber.

* * * * *